(12) United States Patent
Holmström

(10) Patent No.: US 8,140,157 B2
(45) Date of Patent: Mar. 20, 2012

(54) MEDICAL DEVICE FOR DETECTING ISCHEMIA AND A METHOD FOR SUCH A DEVICE

(75) Inventor: Nils Holmström, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 417 days.

(21) Appl. No.: 12/528,467

(22) PCT Filed: Feb. 28, 2007

(86) PCT No.: PCT/SE2007/000195
§ 371 (c)(1),
(2), (4) Date: Aug. 25, 2009

(87) PCT Pub. No.: WO2008/105692
PCT Pub. Date: Sep. 4, 2008

(65) Prior Publication Data
US 2010/0100147 A1    Apr. 22, 2010

(51) Int. Cl.
*A61N 1/00* (2006.01)
(52) U.S. Cl. ......................................... 607/17
(58) Field of Classification Search ................. 424/464, 424/93.7; 600/407, 508, 547; 607/17
See application file for complete search history.

(56) References Cited

U.S. PATENT DOCUMENTS

| | | | |
|---|---|---|---|
| 4,458,694 A * | 7/1984 | Sollish et al. ................ | 600/547 |
| 5,282,840 A | 2/1994 | Hudrlik | |
| 5,454,377 A | 10/1995 | Dzwoncayk et al. | |
| 5,807,272 A | 9/1998 | Kun et al. | |
| 6,115,628 A | 9/2000 | Stadler et al. | |
| 6,256,538 B1 | 7/2001 | Ekwall | |
| 6,473,640 B1 | 10/2002 | Erlebacher | |
| 6,501,984 B1 | 12/2002 | Church et al. | |
| 6,604,000 B2 | 8/2003 | Lu | |
| 6,752,765 B1 | 6/2004 | Jensen et al. | |
| 7,294,334 B1 * | 11/2007 | Michal et al. ................ | 424/93.7 |
| 2003/0216630 A1 * | 11/2003 | Jersey-Willuhn et al. .... | 600/407 |
| 2005/0080460 A1 | 4/2005 | Wang et al. | |
| 2006/0184060 A1 | 8/2006 | Belalcazar et al. | |
| 2006/0235326 A1 | 10/2006 | Dzwonczyk et al. | |

(Continued)

FOREIGN PATENT DOCUMENTS
WO    WO 2004/105862    12/2004
WO    WO 2006/119015    11/2006

OTHER PUBLICATIONS

Chapter 26, Impedance Tomography, Bioelectromagnetism: Principles and Applications of bioelectric and Biomagnetic Fields, Malmivuo et al. (1995) pp. 420-427.

(Continued)

*Primary Examiner* — George Manuel
*Assistant Examiner* — Robert Wieland
(74) *Attorney, Agent, or Firm* — Schiff Hardin LLP

(57) ABSTRACT

In a method and medical device for detecting an ischemic episode and to determine a location of ischemia in a heart of a patient, an impedance measuring circuit measures the impedances in the tissue between electrodes of at least one electrode configuration according to a predetermined measurement scheme and an ischemia detector evaluates the measured impedance values using at least one reference impedance image of the heart to detect changes in the measured impedances that are consistent with an ischemia and to determine a location of the ischemia to at least one region of the image.

43 Claims, 7 Drawing Sheets

U.S. PATENT DOCUMENTS

2006/0241357 A1  10/2006  Chirife
2007/0043393 A1   2/2007  Brockway et al.
2007/0232943 A1*  10/2007  Harel et al. ................ 600/508
2009/0143690 A1   6/2009  Bjorling et al.

OTHER PUBLICATIONS

"Finite Element Method and Reconstruction Algorithms in Electrical Impedance Tomography," Woo "Anals of Biomedical Engineering," vol. f19, No. 2 (1991) pp. 228-229.

"A Fast Image Reconstruction Algorithm for Electrical Impedance Tomography," Kuzuoglu et al, Pysiol. Meas., vol. 15 (1994) pp. A115-A124.

"A Regularised Electrical Impedance Tomography Reconstruction Algorithm," Hua et a, Clin. Phys. Physiol. Meas. vol. 9, Suppl. A (1988) pp. 137-141.

US 2006/0087870, May 2004, Jarverud (withdrawn).

* cited by examiner

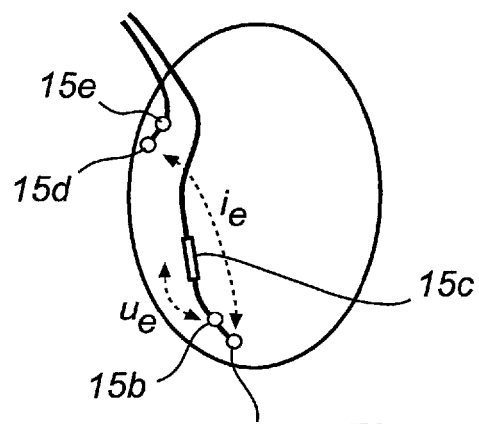 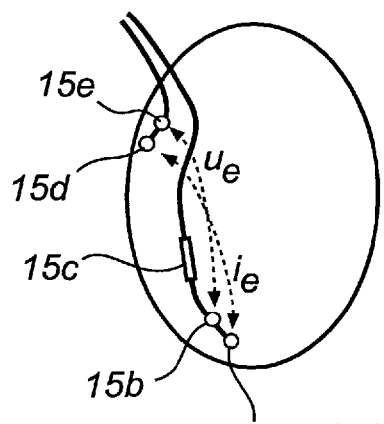
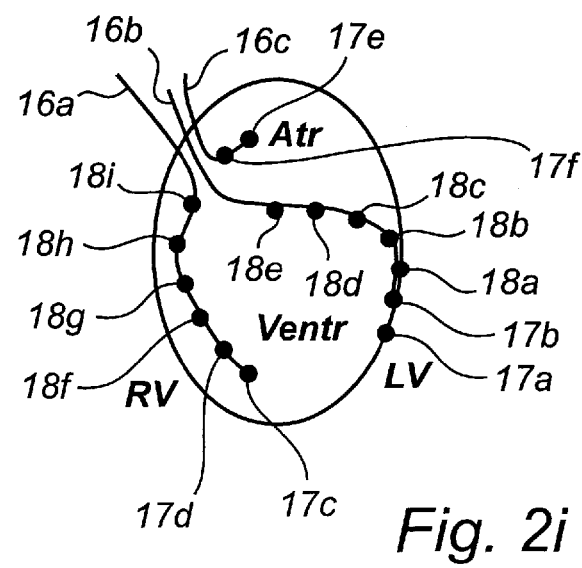

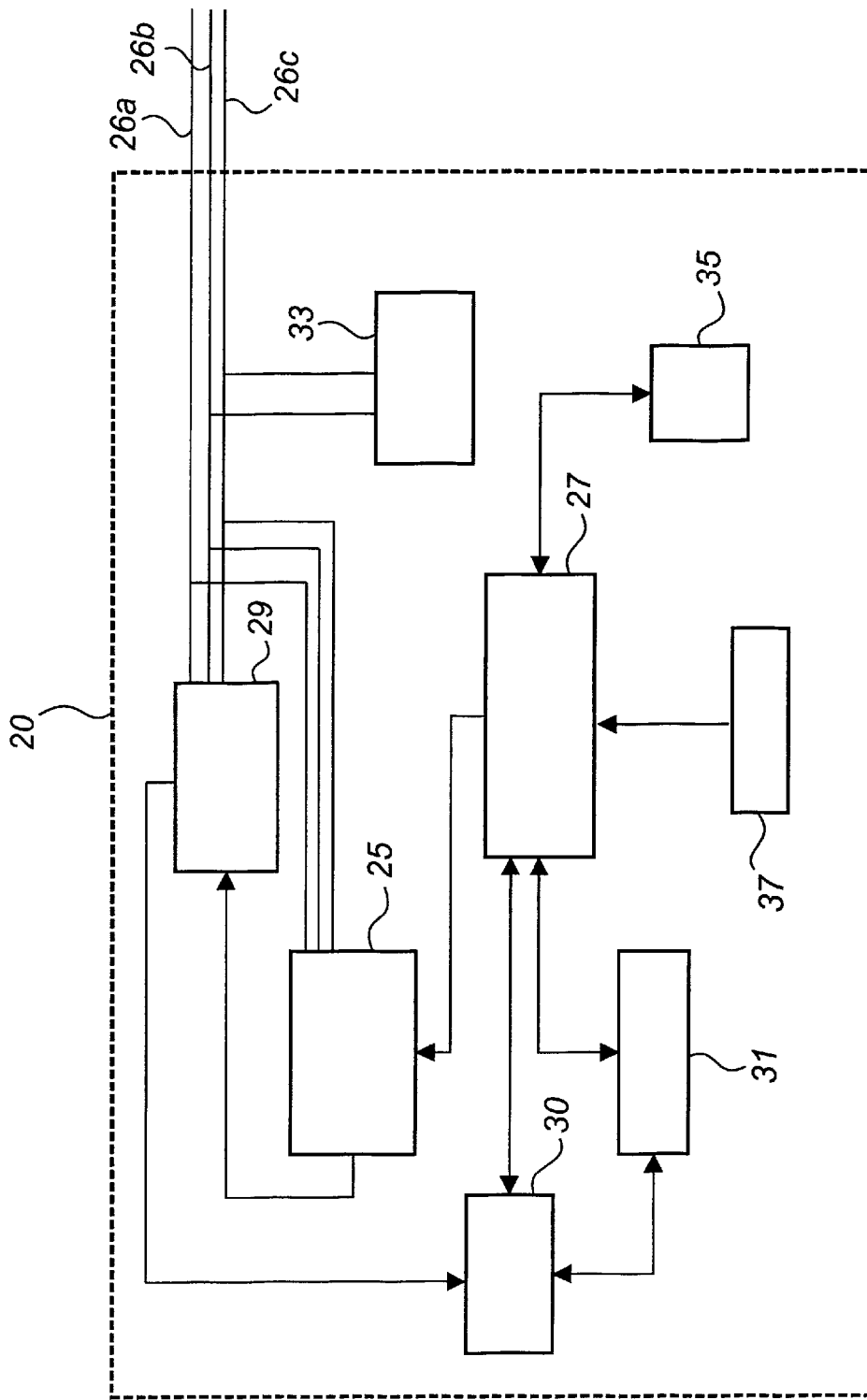

MEDICAL DEVICE FOR DETECTING ISCHEMIA AND A METHOD FOR SUCH A DEVICE

BACKGROUND OF THE INVENTION

1. Field of the Invention

The present invention generally relates to cardiac pacing systems and, in particular, to methods and medical devices for detecting an ischemic episode and to determine a location of ischemia in a heart of a patient.

2. Description of the Prior Art

Due to the in general poorer medical status of pacemaker and ICD patients they are subjected to an increased risk of ischemic heart disease (IHD) and myocardial infarction (MI). Ischemic heart disease can be divided into unstable and stable ischemia. Unstable ischemia is a highly life-threatening situation most often caused by an infarction of one or several coronary arteries. Sudden cardiac death depends in 90% of all cases on IHD. The possibility to survive depends on how fast the patient gets relevant treatment. Stable ischemia is very common among elderly people and the mortality is low or moderate. There is both silent ischemia and ischemia with heart pain, i.e. angina pectoris. The most common reason is arteriosclerosis in the coronary vessels. It can be treated with drugs or operatively using bypass techniques, stents, etc. When IHD progresses it may lead to myocardial infarction (MI), congestive heart failure (CHF) and/or the patients death. In fact early detection of IHD can serve as an early marker for CHF risk factor. An early detection of ischemic heart disease is thus required since that will give opportunities to prevent life threatening complications.

In light of this, a number of approaches have been made to detect ischemia with implantable medical devices such as pacing devices using the impedance of tissue. For example, in US 2006/0241357, a method and device for detecting the occurrence of ischemia using measurements of end-systolic impedances. However, a determination of a more specific location of the detected ischemia is not described US 2006/0241357.

Furthermore, in WO 93/18821 a monitoring system for monitoring the condition of a patient's body tissue, for example, to detect ischemia. The impedance of tissue between electrodes is measured for a number of different frequencies and an impedance signature is created. Ischemia causes a shift in this signature and thus the onset of ischemia can be detected by evaluating changes in the impedance signature. A more specific detection of the location of the ischemia is not described in WO 93/18821.

Furthermore, EP 1 690 566 corresponding to US 2006/0241357, U.S. Pat. No. 6,604,000 and U.S. Pat. No. 6,256,538 also present implantable medical devices incorporating an ischemia detector responsive to measured intracardiac impedance.

Thus, it remains a need within the art of a method and medical device that are capable of detecting the occurrence an ischemic episode and of determining a location of the ischemia.

SUMMARY OF THE INVENTION

An object of the present invention is to detect the occurrence of an ischemic episode and to determine the location of the ischemia.

According to another object of the present invention, the occurrence of an ischemic episode is automatically detected and a location of the ischemia is automatically determined.

According to a further object of the present invention, a commencement of an ischemic episode can be detected at an early stage and the location of the ischemia can be determined at an early stage.

According to an aspect of the present invention, there is provided an implantable medical device including a pulse generator adapted to produce cardiac stimulating pulses and being connectable to at least one medical lead for delivering the pulses to cardiac tissue of a heart of a patient. The implantable medical device comprises an impedance measuring circuit adapted to, during impedance measurement sessions, generate electrical signals to be applied between electrodes of at least two electrode configurations according to a predetermined scheme; and to measure the impedances in the tissue between the electrodes of the at least two electrode configurations to the applied electrical signals according to the predetermined scheme. Further, the implantable medical device comprises an ischemia detector adapted to evaluate the measured impedance values including comparing the measured impedances with at least one reference impedance image of the heart comprising a number of impedance regions to detect changes in the measured impedances being consistent with an ischemia and to determine a location of the ischemia to at least one of the regions.

According to a second aspect of the present invention, there is provided a method for implantable medical device including a pulse generator adapted to produce cardiac stimulating pulses and being connectable to at least one medical lead for delivering the pulses to cardiac tissue of a heart of a patient. The method comprises the steps of generating, during impedance measurement sessions, electrical signals to be applied between electrodes of at least two electrode configurations according to a predetermined scheme; measuring the impedances in the tissue between the at least first electrode and the at least second electrode of the electrode configurations to the applied electrical signals; and evaluating the measured impedance values including comparing the measured impedances with at least one reference impedance image of the heart comprising a number of impedance regions to detect changes in the measured impedances being consistent with an ischemia and to determine a location of the ischemia to at least one of the regions.

According to a further aspect of the present invention, there is provided a computer-readable medium, directly loadable into an internal memory of an implantable medical device according to the first aspect of the present invention, comprising software code portions for causing the implantable medical device to perform steps in accordance with the second aspect of the present invention.

The invention utilizes electrical bio-impedance (EBI) to monitor the heart and impedance imaging to detect an ischemic episode and to determine a location of the ischemia. The impedance is measured in a number of electrode configurations. Electric current may be fed consecutively by different electrode pairs and the corresponding voltage may be measured consecutively by all remaining electrode pairs. Thereby, it is possible to create an image of the impedance of different regions of the heart. Thus, the invention is based on the discoveries that the impedance spectrum undergoes significant and characteristic changes in the course of ischemia and that obtained impedance matrices can be used to create an image of the heart which, in turn, can be used to detect and locate an ischemia. Due to the fact that an ischemic episode can be detected before the patient actually feels any symptoms it is possible to initiate a therapy at an early stage, i.e. before the angina attack.

According to an embodiment of the present invention, the ischemia detector is adapted to create a present impedance image using the measured impedance values, which impedances are measured in accordance with the predetermined scheme, and to compare the present impedance image with the reference impedance image to detect changes in the measured impedances being consistent with an ischemia and to determine a location of the ischemia to at least one of the regions.

In another embodiment, the impedance measuring circuit is adapted to perform reference measurement sessions to obtain reference impedances for the electrode configurations in accordance with the predetermined scheme and the ischemia detector is adapted to create the reference impedance images using the measured reference impedances. In one certain embodiment, the impedances are measured at normal conditions and at provoked ischemic episodes. Thereby, it is possible to create one reference impedance image for normal conditions and one reference impedance image for ischemic episodes, which thus enables the ischemia detector to identify or detect an ischemic episode with a high degree of accuracy and reliability by comparing an impedance image created by just previously measured impedances.

In embodiments of the present invention, electric current is fed consecutively through different electrode pairs and corresponding voltage is measured consecutively by the remaining electrode pairs in a predetermined order or scheme including the so called neighboring method, the so called cross method, the so called opposite method, and the so called adaptive method. These methods, as well as other methods that can be used in connection with the present invention, are described in "Bioelectromagnetism: Principles and applications of bioelectric and biomagnetic fields", Malmivuo J. and Plonsey R., Oxford University Press, 1995, (chapter 26), which hereby is incorporated by reference.

According to an embodiment, the ischemia detector is adapted to, from the collected impedance data, construct an image of the distribution of the electric impedance by use of reconstruction algorithms. Such algorithms are discussed in detail in, for example, "A regularised electrical impedance tomography reconstruction algorithm", P. Hua P, Webster J. G., and Tompkins W. J., 1988, Clin. Phys. Physiol. Meas. 9, 137-141, "A fast image reconstruction algorithm for electrical impedance tomography", Kuzuoglu M. et al., 1994, Physiol. Meas. 15, A115-A124, or "Finite fast image reconstruction algorithm for electrical impedance tomography", Eung J. W., and Webster J. G., 1991, Annals of Biomedical Engineering, Vol. 19, No. 2, March.

According to an embodiment, the electrode configurations used to measure the impedance comprise the lead electrodes of an implanted pacemaker or ICD and the device can as well as additional electrodes, whereby the specificity can be improved. A number of additional electrodes, e.g. an array of electrodes, are used to increase a spatial resolution of the measured impedances to identify areas or regions with ischemia.

In accordance with embodiments of the present invention, the electrodes are arranged on medical leads located in one, some of, or all of the following: a coronary vein in the left ventricle or in the left atrium, in the right atrium, in the right ventricle, and/or in or at the epicardium, and/or on the can of the implantable medical device.

According to an embodiment of the present invention, the impedance measuring circuit is adapted to generate electrical signals at least at a first frequency and at a second frequency and to measure the impedance in the tissue between the at least a first electrode and the at least a second electrode of the electrode configurations at the at least first frequency and the at least second frequency and the ischemia detector is adapted to evaluate the measured impedances including comparing the measured impedances at the first frequency with impedance images for the first frequency of the heart each including a number of impedance regions and comparing the measured impedances at the second frequency with impedance images for the second frequency of the heart each including a number of impedance regions, the regions of the impedance image at the second frequency substantially corresponding to the regions of the impedance image at the first frequency, to detect changes in the measured impedances being consistent with an ischemia and to determine a location of the ischemia to at least one of the regions.

In a further embodiment of the present invention, the impedance measuring circuit is adapted to generate electrical signals across a band of frequencies including the first and second frequencies.

In yet another embodiment of the present invention, the ischemia detector is adapted to determine a trend of the real part of the measured impedance over time and/or a trend of the imaginary part of the measured impedance over time for each region of the impedance image. Further, the ischemia detector is adapted to determine an increase in the real part of the impedance over time within a predetermined period of time above a first predetermined threshold and/or a decrease in the imaginary part within a predetermined interval of time below a second predetermined threshold as being consistent with an ischemia and to determine a location of the ischemia to at least one region for which a time derivative of the real part is above the first predetermined threshold and/or a time derivative of the imaginary part of the impedance is below the second predetermined threshold. Alternatively, the ischemia detector is adapted to determine a location of the ischemia to a region for which a time derivative of the real part is the highest and/or a time derivative of the imaginary part of the impedance is the lowest.

According another embodiment, the ischemia detector is adapted to determine a trend of the real part of the measured impedance at the first frequency and the second frequency, respectively, over time for each region of the impedance image and/or a trend of the imaginary part of the measured impedance at the first frequency and the second frequency, respectively, over time for each region of the impedance image. The real part at the first frequency and the second frequency, respectively, are compared at a predetermined point of time and/or the imaginary part at the first frequency and the second frequency, respectively, are compared at the predetermined point of time. Further, an absolute value of a quotient between the real part at the first frequency and the real part at the second frequency being above a first predetermined quotient threshold and/or an absolute value of a quotient between the imaginary part at the first frequency and the imaginary part at the second frequency being above a second predetermined quotient threshold is/are determined to be consistent with an ischemia and a location of the ischemia is determined to at least one region for which the absolute value of the quotient between the real part at the first frequency and the real part at the second frequency is above a first predetermined quotient threshold and/or the absolute value of the quotient between the imaginary part at the first frequency and the imaginary part at the second frequency is above a second predetermined quotient threshold. In an alternative embodiment, the ischemia detector is adapted to determine a location of the ischemia to a region for which the absolute value of the quotient between the real part at the first frequency and the real part at the second frequency is the highest and/or the absolute value of the quotient between the imaginary part at the first frequency and the imaginary part at the second frequency is the highest.

In accordance with a further embodiment, the ischemia detector is adapted to determine a trend of the phase angle of the impedance at a predetermined frequency over time, to determine an increase of the phase angle within a predetermined interval of time above a predetermined threshold as being consistent with an ischemia and to determine a location of the ischemia to at least one region for which a time derivative of the phase angle is above the predetermined threshold. Alternatively, the ischemia detector is adapted to determine a location of the ischemia to a region for which a time derivative of the phase angle is the highest.

Furthermore, the medical device according to an embodiment of the present invention comprises an activity sensor adapted to measure an activity level of the patient and wherein the ischemia detector is adapted to determine whether the measured activity level is below a predetermined activity level limit and to use this determination when evaluating the measured impedances. Thereby, the reliability and accuracy of the detection can be improved. An initial reaction of an ischemia is a global stress reaction with release of adrenaline etc and increased contractility and heart rate, which affects the impedance, and similar reactions may occur due to increased workload. Therefore, by sensing the activity level of the patient, the accuracy of the detection can be enhanced since a reaction caused by increased workload can be distinguished from a true ischemia episode.

According to an embodiment of the present invention, other physiological parameters such as heart rate, body temperature and/or minute ventilation are measured and used in the detection of an ischemic episode. Thereby, the accuracy and reliability of the detection can be improved even further.

In another embodiment of the present invention, the impedance measuring circuit is adapted to synchronize the impedance measurements with cardiac cycles of the patient such that the impedance measurements are performed at substantially the same point of time in the cardiac cycles, for example, during end-diastole.

In further embodiments of the present invention, the impedance measuring circuit is adapted to perform each impedance measurement session over a predetermined number of consecutive cardiac cycles and to calculate each impedance value as a mean value over the predetermined number of cardiac cycles.

According to an embodiment of the present invention, the implantable medical device comprises a posture detecting circuit connected to the impedance measuring circuit and being adapted to detect at least a predetermined posture of the patient. The impedance measuring circuit is adapted to initiate the impedance measuring sessions when the patient is in the at least one predetermined posture.

According to embodiments of the present invention, at the detection of an ischemic episode, the pacemaker therapy may be adapted to the stressed situation. The pacing rate may be set to a rest rate in order to increase the diastolic interval and the myocardial blood supply. The pacing amplitudes should be increased and an AutoCapture™ function may be turned off to avoid loss of capture. The present invention may thus improve the patient's comfort and work capacity when necessary at the detection of an ischemic episode.

In a further embodiment of the present invention, a notification or warning including the ischemia data, e.g. including the identification of the ischemia, the point of time at which the ischemia episode was identified and the location of the ischemia, is transferred to one or more external devices, for example, a user equipment, a home monitoring unit, a remote monitoring unit or an emergency server at a care institution or the local hospital via a RF telemetry communication unit of the medical device and at least one external radio communication network such as wireless LAN ("Local Area Network"), GSM ("Global System for Mobile communications"), or UMTS ("Universal Mobile Telecommunications System"). For a given communication method, a multitude of standard and/or proprietary communication protocols may be used. For example, and without limitation, wireless (e.g. radio frequency pulse coding, spread spectrum frequency hopping, time-hopping, etc.) and other communication protocols (e.g. SMTP, FTP, TCP/IP) may be used. Other proprietary methods and protocols may also be used. The notification may include at least the patient identity, the occurrence of a myocardial infarction and/or the location of the detected infarct within the heart. The communication unit may be adapted to communicate with the user equipment, e.g. mobile phone, a pager or a PDA ("Personal Digital Assistant"), which is adapted to receive the notification via, for example, Bluetooth and to transmit it via the communication network further on to the medical care institution. Alternatively, the communication unit may be adapted to communicate with a home monitoring unit located in the home of the patient via, for example, Bluetooth. The home monitoring unit may be adapted to communicate with the care institution via a telephone link, or via the communication network as described above.

Furthermore, the notification may include a geographical location of the patient, for example, by means of a GPS ("Global Positioning System") unit arranged in the user equipment. Thereby, it is possible for the care institution to obtain an early notification of the infarct of a patient and, additionally, the position of the patient and hence the patient can be given care at an early stage of an ischemia.

The patient may also or additionally be informed or notified of the detection of an ischemic episode by means of a vibration unit of the implantable medical device, which unit is caused to vibrate at a certain frequency at the detection of the ischemic episode.

As realized by the person skilled in the art, steps of the methods of the present invention, as well as preferred embodiment thereof, are suitable to realize as a computer program or a computer readable medium.

BRIEF DESCRIPTION OF THE DRAWINGS

The features that characterize the invention, both as to organization and to method of operation, together with further objects and advantages thereof, will be better understood from the following description used in conjunction with the accompanying drawings. It is to be expressly understood that the drawings is for the purpose of illustration and description and is not intended as a definition of the limits of the invention. These and other objects attained, and advantages offered, by the present invention will become more fully apparent as the description that now follows is read in conjunction with the accompanying drawings.

FIGS. 2a-2i schematically show embodiments of electrode configurations in accordance with the present invention.

FIG. 3 schematically illustrates an embodiment of the implantable medical device according to the present invention.

DESCRIPTION OF THE PREFERRED EMBODIMENTS

In the following, the present invention will be discussed in the context of medical systems comprising at least an implantable pacemaker, and medical leads such as an atrial lead and a ventricular lead.

Figure 1:
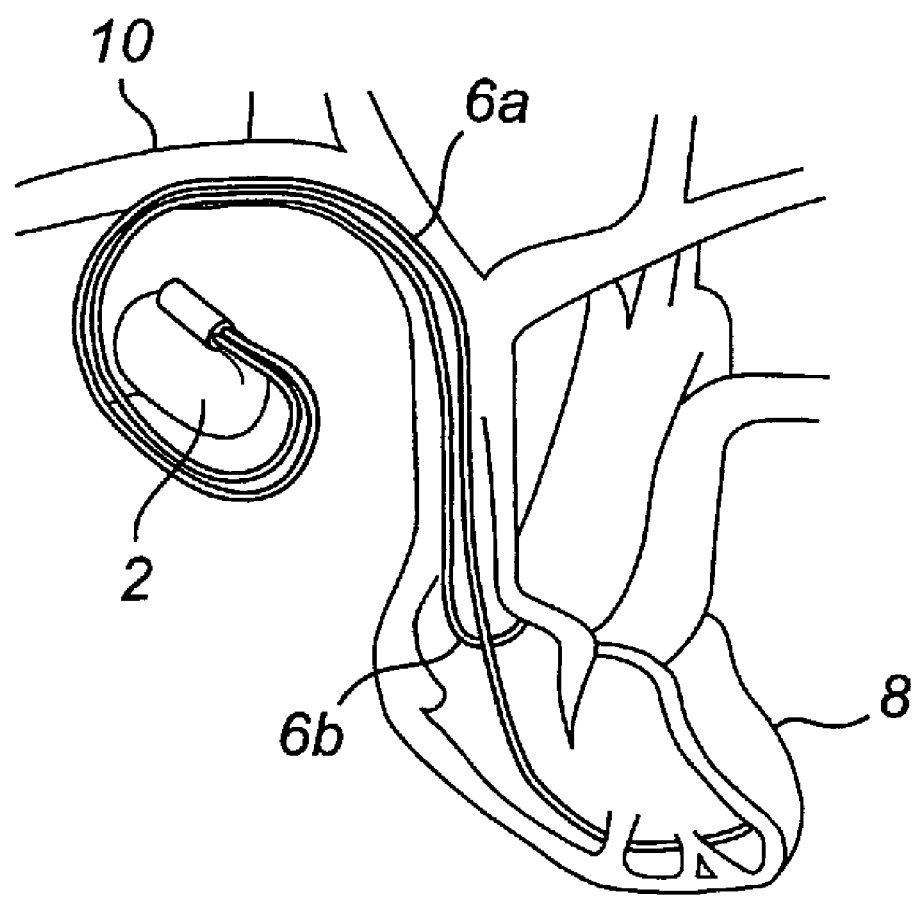
FIG. 1 schematically shows an embodiment of a pacemaker system in which an implantable medical device in accordance with the present invention may be implemented.

With reference to FIG. 1 there is shown a schematic diagram of a medical device implanted in a patient in which device the present invention can be implemented. As seen, this embodiment of the present invention is shown in the context of a pacemaker 2 implanted in a patient (not shown). The pacemaker 2 comprises a housing being hermetically sealed and biological inert. Normally, the housing is conductive and may, thus, serve as an electrode. One or more pacemaker leads, where only two are shown in FIG. 1 namely a right ventricular lead 6a and an atrial lead 6b, are electrically coupled to the pacemaker 2 in a conventional manner. The leads 6a, 6b extend into the heart 8 via a vein 10 of the patient. One or more conductive electrodes for receiving electrical cardiac signals and/or for delivering electrical pacing to the heart 8 are arranged near the distal ends of the leads 6a, 6b. As the skilled man in the art realizes, the leads 6a, 6b may be implanted with its distal end located in either the atrium or ventricle of the heart 8. The pacemaker leads are normally implanted via a jugular or cephalic vein to vena cava superior and the right atrium and right ventricle. The electrode configuration according to the present invention schematically shown may have a number of additional electrodes to the pacing electrodes in order to provide impedance data for obtaining an impedance image of the heart having a higher degree of resolution. The impedance can be obtained by means of bipolar, tripolar or quadropolar measurements, which will be described with reference to FIGS. 2a-2i. A bipolar measurement is a measurement where the electrical alternating current is applied between two electrodes and the voltage response is measured between the same electrodes. If only one electrode is common, it is called a tripolar measurement and if all four electrodes are different it is called a quadropolar measurement.

Figure 2A:
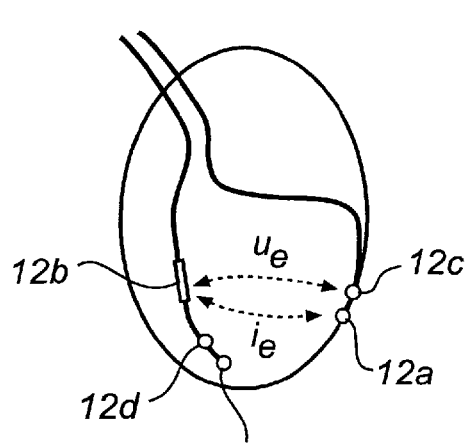
Figure 2B:
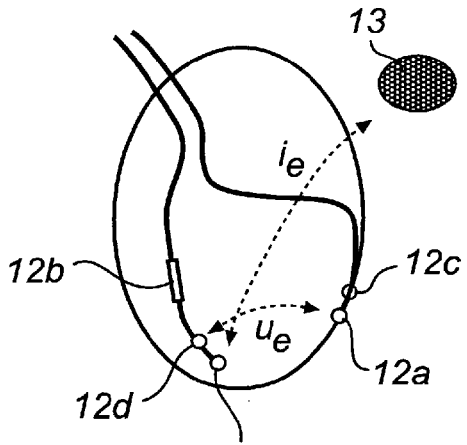

Turning now to FIGS. 2a-2i, a number of different measurement settings will be discussed. In FIG. 2a, a tripolar measurement setting is shown where the excitation current $i_e$ is applied between a left ventricular tip electrode 12a and a right ventricular coil electrode 12b and the resulting voltage $u_e$ is measured between a left ventricular ring electrode 12c and the right ventricular coil electrode 12b. Further, the electrode configuration includes a right ventricular ring electrode 12d and a right ventricular tip electrode 12e. In FIG. 2b, a quadropolar measurement setting is shown where the excitation current $i_e$ is applied between the right ventricular tip electrode 12f and a case 13 of a medical device and the voltage $u_e$ is measured between the right ventricular ring electrode 12d and the left ventricular tip electrode 12a.

Figure 2C:
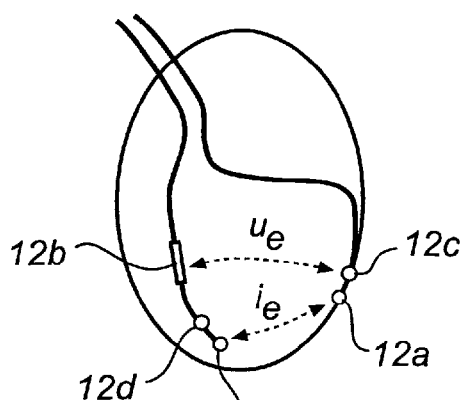
Figure 2D:
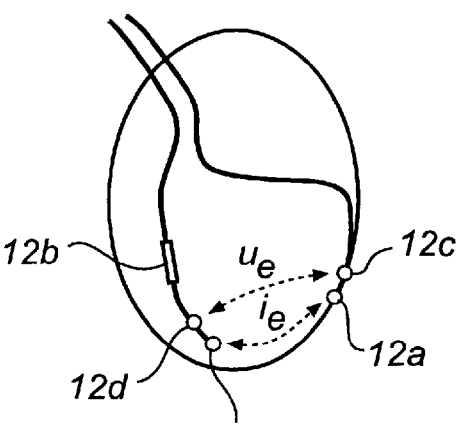

In FIG. 2c and FIG. 2d, measurement settings being particularly efficient for measuring left ventricular contractions and thus for creating impedance images of the left ventricle are shown. In FIG. 2c, a quadropolar setting is shown where the excitation current $i_e$ is applied between the right ventricle tip electrode 12e and the left ventricle tip electrode 12a and the resulting voltage $u_e$ is measured between the right ventricle coil electrode 12b and the left ventricle ring electrode 12c. In FIG. 2d, a quadropolar setting is shown where the excitation current $i_e$ is applied between the right ventricular tip electrode 12e and the left ventricle tip electrode 12a and the resulting voltage $u_e$ is measured between the right ventricle ring electrode 12d and the left ventricle ring electrode 12b.

Figure 2E:
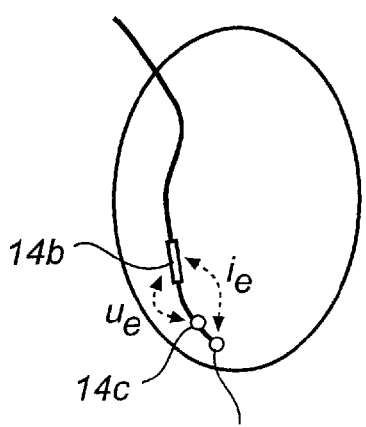
Figure 2F:
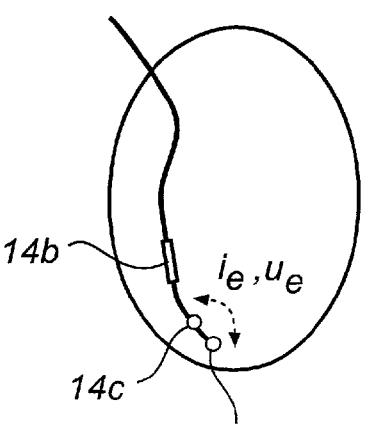

In FIGS. 2e-2h, measurement settings being particularly efficient for measuring volume variations in the right ventricle and thus for creating impedance images of the left ventricle are shown. In FIG. 2e, a tripolar setting is shown where the excitation current $i_e$ is applied between a right ventricle tip electrode 14a and a right ventricle coil electrode 14b and the resulting voltage $u_e$ is measured between a right ventricle ring electrode 14c and the right ventricle coil electrode 14b. In FIG. 2f, bipolar setting is shown where the excitation current $i_e$ is applied between the right ventricle tip electrode 14a and the right ventricle ring electrode 14c and the resulting voltage $u_e$ is measured between the same electrodes. In FIG. 2g, a quadropolar setting is shown where the excitation current $i_e$ is applied between a right ventricle tip electrode 15a and a right atrium tip electrode 15d and the resulting voltage $u_e$ is measured between a right ventricle ring electrode 15b and a right ventricle coil electrode 15c. In FIG. 2h, a quadropolar setting is shown where low voltage leads are shown. The excitation current $i_e$ is applied between the right ventricle tip electrode 15a and the right atrium tip electrode 15d and resulting voltage $u_e$ is measured between the right ventricle ring electrode 15b and a right atrium ring electrode 15e.

In FIG. 2i yet another electrode configuration according to the present invention including a right ventricular lead 16a, a left ventricular lead 16b, and right atrium lead 16c. Each of the leads comprises additional electrodes 18a-18i in addition to ordinary pacing electrodes 17a-17f.

The spatial resolution of the impedance measurements may be enhanced by using an array of electrodes, for example, any one of the electrode configurations described above. According to the present invention, electric current is fed consecutively through different electrode pairs and corresponding voltage is measured consecutively by the remaining electrode pairs. Thereby, it is possible to, using reconstruction algorithms, create an image of the impedance of different regions of the volume conductor, i.e. the heart or a part of the heart. The image can be created by means of impedance tomography. The impedance can be measured by means of a number of methods including the so called neighboring method, the so called cross method, the so called opposite method, and the so called adaptive method. These methods, as well as other methods that can be used in connection with the present invention, are described in "Bioelectromagnetism: Principles and applications of bioelectric and biomagnetic fields", Malmivuo J. and Plonsey R., Oxford University Press, 1995, (chapter 26). From the collected impedance data, an image of the distribution of the electric impedance can be constructed by use of certain reconstruction algorithms. Such algorithms are discussed in detail in, for example, "A regularised electrical impedance tomography reconstruction algorithm", P. Hua P, Webster J. G., and Tompkins W. J., 1988, Clin. Phys. Physiol. Meas. 9, 137-141, "A fast image reconstruction algorithm for electrical impedance tomography", Kuzuoglu M. et al., 1994, Physiol. Meas. 15, A115-A124, or "Finite fast image reconstruction algorithm for electrical impedance tomography", Eung J. W., and Webster J. G., 1991, Annals of Biomedical Engineering, Vol. 19, No. 2, March.

As the skilled person realizes, the above given electrode configurations are only exemplary and there are thus a number of other conceivable configurations within the scope of the present invention. For example, in yet another embodiment, leads with arrays of electrodes are placed free-flowing in a vein/artery and may be used with the can or housing the implantable medical device. Further, an array of electrodes arranged on a lead may be located on the epicardium, which may be used in addition to any one of the above given configurations described with reference to FIGS. 2a-2i.

With reference now to FIG. 3, the configuration including the primary components of an embodiment of an implantable medical device according to the present invention will be described. The illustrated embodiment includes an implantable medical device 20, such as the pacemaker shown in FIG. 1, and leads 26a, 26b and 26c, for example, a right ventricular lead, a left ventricular lead, and right atrium lead, respectively, for delivering signals between the implantable medical device 20 and tissue of the heart. The leads 26a, 26b, 26c may be unipolar or bipolar, and may include any of the passive or active fixation means known in the art for fixation of the lead to the cardiac tissue. As an example, the lead distal tip (not shown) may include a tined tip or a fixation helix. The leads 26a, 26b, 26c comprises one or more electrodes (as described with reference to FIGS. 2a-2i), such tip electrodes, ring electrodes, coil electrodes, arranged to, inter alia, transmit pacing pulses for causing depolarization of cardiac tissue adjacent to the electrode(-s) generated by a pace pulse generator 25 under influence of a control circuit 27 comprising a microprocessor. The control circuit 27 controls, inter alia, pace pulse parameters such as output voltage and pulse duration.

Moreover, an impedance circuit 29 is adapted to carry out impedance measurements of the tissue of the heart of the patient. The impedance circuit 29 is arranged to apply excitation current pulses between electrodes of respective electrode configurations including at least a first electrode and at least a second electrode according to a predetermined measurement scheme, i.e. according to any one of the methods described above including the so called neighboring method, the so called cross method, the so called opposite method, or the so called adaptive method. The impedances in the tissue between the electrodes of the at least one electrode configuration to the applied electrical signals is measured according to the predetermined scheme. As discussed above, the electrodes can be arranged in a number of electrode configurations in medical leads connected to the implantable medical device 20. During an impedance measurement session, a number of impedance values are obtained and stored in an impedance matrix according to the predetermined measurement scheme. The measurement sessions may be synchronized with cardiac cycles of the patient such that the impedance measurements are performed at substantially the same point of time in the cardiac cycles, for example, during end-diastole. Further, each impedance measurement session can be performed over a predetermined number of consecutive cardiac cycles and each impedance value may thus be calculated as a mean value over the predetermined number of cardiac cycles.

Furthermore, the impedance circuit 29 is coupled to an ischemia detector 30 adapted to evaluate the measured impedance values, i.e. the obtained impedance matrix, including comparing the measured impedances with a reference impedance image of the heart having a number of impedance regions to detect changes in the measured impedances being consistent with an ischemia and to determine a location of the ischemia to at least one of the regions. The detection and location determination of ischemia will be discussed in more detail below with reference to FIGS. 6a-6c. The reference impedance image may be created by the ischemia detector by at least one reference impedance matrix obtained by a reference measurement session. The impedance images are created using reconstruction algorithms as described above.

Further, a memory circuit 31 is connected to the ischemia detector and the control circuit 27, which memory circuit 31 may include a random access memory (RAM) and/or a non-volatile memory such as a read-only memory (ROM). For example, the reference impedance matrix and obtained impedance values may be stored in the memory circuit 31. Detected signals from the patient's heart are processed in an input circuit 33 and are forwarded to the microprocessor of the control circuit 27 for use in logic timing determination in known manner. Furthermore, the implantable medical device 20 according to the present invention may include an activity sensor 37 adapted to measure an activity level of the patient, for example, an accelerometer. The implantable medical device 20 is powered by a battery (not shown), which supplies electrical power to all electrical active components of the medical device 20. Data contained in the memory circuit 31 can be transferred to a programmer (not shown) via a telemetry communication unit 35 of the implantable medical device 20 and a programmer interface (not shown) for use in analyzing system conditions, patient information, etc.

The implantable medical device 20 may further has a posture detecting circuit adapted to detect at least a predetermined posture of the patient. The impedance measuring circuit 29 may be adapted to initiate the impedance measuring sessions when the patient is in the at least one predetermined posture.

According to an embodiment of the present invention, the impedance measuring circuit is adapted to generate electrical signals at least at a first frequency and at a second frequency according to a predetermined measurement scheme, i.e. according to any one of the methods described above including the so called neighboring method, the so called cross method, the so called opposite method, or the so called adaptive method, which circuit will be described in more detail below with reference to FIG. 4. As discussed above, the electrodes can be arranged in a number of electrode configurations in medical leads connected to the implantable medical device 20. Further, the impedance measuring circuit 49 is adapted to measure the impedance in the tissue between the electrodes of the electrode configuration at the at least first frequency and the at least second frequency according to the predetermined scheme. In another embodiment, the impedance measuring circuit is adapted to generate electrical signals across a band of frequencies including the first and the second frequency. The ischemia detector 30 is adapted to evaluate the measured impedances including comparing the measured impedances at the first frequency with an impedance image for the first frequency of the heart including a number of impedance regions and comparing the measured impedances at the second frequency with an impedance image for the second frequency of the heart including a number of impedance regions, wherein the regions of the impedance image at the second frequency substantially correspond to the regions of the impedance image at the first frequency. Thereby, the ischemia detector 30 is capable of detecting changes in the measured impedances being consistent with an ischemia and to determine a location of the ischemia to at least one of the regions. The detection and location determination of ischemia will be discussed in more detail below with reference to FIGS. 6a-6c.

Figure 4:
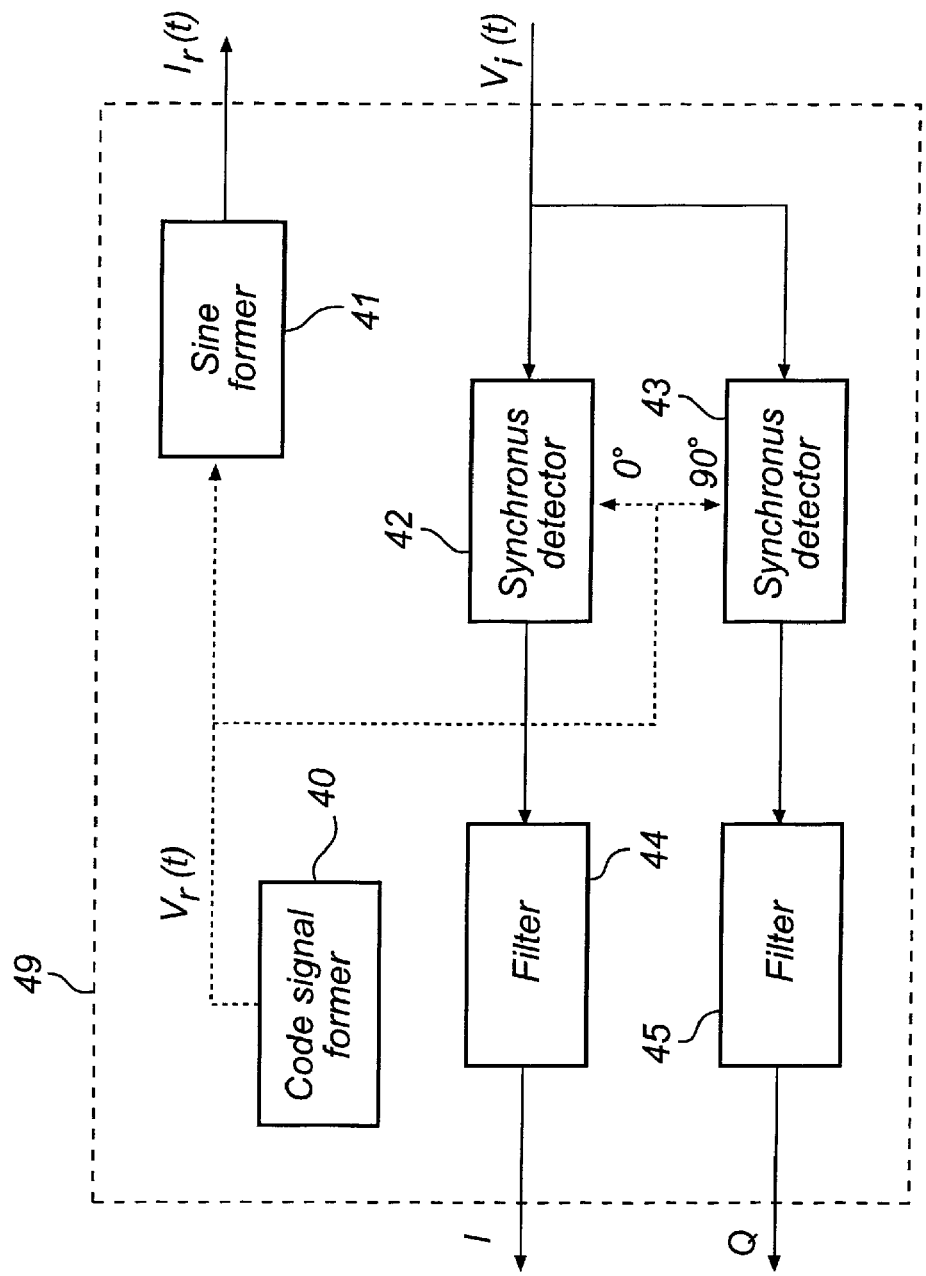
FIG. 4 is block diagram of an embodiment of an impedance circuit for measuring complex impedance.

With reference to FIG. 4, an embodiment of an impedance circuit adapted for measuring complex impedance of the tissue of the heart of the patient will be described in more detail. The impedance measuring circuit 49 includes a code signal former circuit 40 adapted to control the impedance measurements by synchronizing the different circuits of the impedance circuit 49. Alternatively, the code signal former circuit 40 may be arranged in the controller 27. Moreover, the impedance circuit 49 includes a sine former circuit 41 driven by the code signal former circuit 40, which sine former circuit 41 is adapted to deliver a stepwise sine current:

$$I_r = A_r \cdot \sin \omega t \tag{1}$$

to the test object, i.e. the tissue of the heart of the patient. The current is applied between electrodes of an electrode configuration, for example, any one of the configurations described above with reference to FIGS. 2a-2i. The resulting voltage difference at the input of a first synchronous detector 42 and at a second synchronous detector 43 connected to respective electrodes is:

$$V_i(t) = A_i \cdot \sin(\omega_i t + \phi) \tag{2}$$

The first synchronous detector 42 and the second synchronous detector 43 are adapted to perform simultaneous in-phase and quadrature signal processing. The detectors 42 and 43 function as analogue multipliers with mutually quadrature stepwise-approximated harmonic waveforms. The code signal former circuit 40 delivers reference signals to the first synchronous detector 42 and the second synchronous detector 43, respectively, in accordance with:

$$V_r(t) = A_r \cdot \sin \omega_r t \tag{3}$$

for the synchronous (0°) signal and $$V_r(t) = A_r \cdot \cos \omega_r t \tag{4}$$

for the quadrature signal.

In first synchronous detector 42, equation (2) and (3) are multiplied, and the output is:

$$V_i(t) \cdot V_r(t) = \frac{1}{2} A_i A_r \cdot \cos\varphi - \frac{1}{2} A_i A_r \cdot \cos(2\omega t + \varphi) \tag{5}$$

In the second synchronous detector 43, equation (2) and (3) are multiplied, and the output is:

$$V_i(t) \cdot V_r(t) = \frac{1}{2} A_i A_r \cdot \sin\varphi + \frac{1}{2} A_i A_r \cdot \sin(2\omega t + \varphi) \tag{6}$$

Both DC and AC components of the multiplications (5) and (6) contain the impedance information but only the first component is used in this embodiment. The second component (double frequency pulsation) is filtered out by low-pass filtering in a first low-pass filter 44 and a second low-pass filter 45 connected to the first synchronous detector 42 and the second synchronous detector 43, respectively. The resulting signals at the output is:

$$V_{OI}(t) = V_i(t) \cdot \overline{V}_r(t) = \frac{A_i A_r}{2} \cos\varphi \tag{7}$$

for the synchronous component and:

$$V_{OQ}(t) = V_i(t) \cdot \overline{V}_r(t) = \frac{A_i A_r}{2} \sin\varphi \tag{8}$$

for the quadrature component.

Equation (7) and (8) are the real and imaginary values for the impedance vector and hence reflects the resistive component and the reactance component, respectively, of the impedance. The impedance values of the different electrodes of the electrode configuration can be utilized by the ischemia detector to create the impedance images using the reconstruction algorithm as discussed above.

Figure 5:
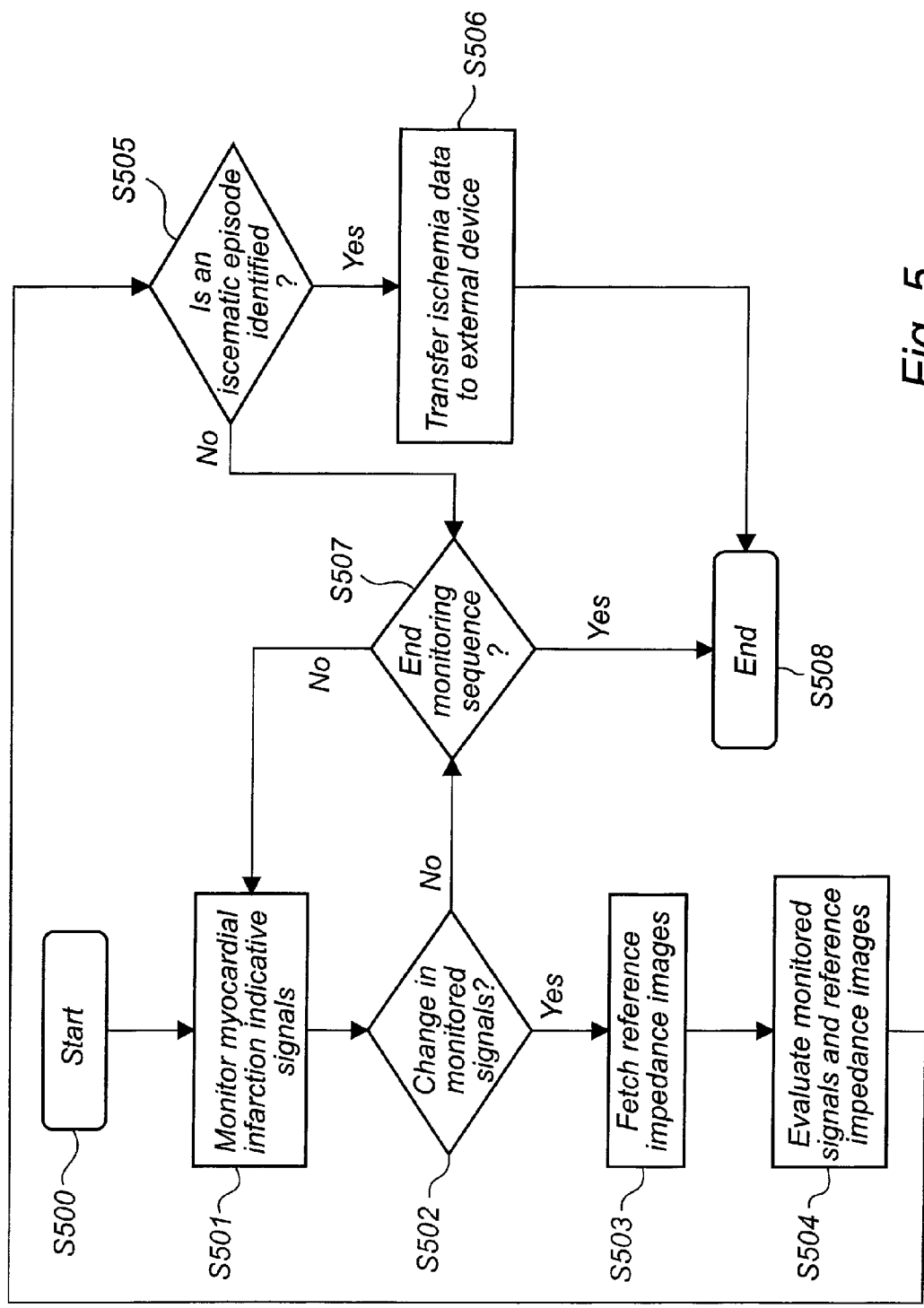
FIG. 5 is high-level flow chart of an embodiment of the method for detecting ischemia according to the present invention.

Referring now to FIG. 5, a high-level flow chart illustrating an embodiment of the method for detecting and locating an ischemic episode using an implantable medical device according to the present invention will be discussed. First, at step S500, the detecting procedure is initiated. The procedure may be initiated at regular intervals or at receipt of a initiation request from an external device via the RF telemetry communication unit 35 of the implantable medical device 20. The external device may be a handheld user equipment such as a mobile phone or a personal digital assistant, which device may communicate with the implantable medical device 20 by means of, for example, Bluetooth. Further, the external device may be a home monitoring unit or programmer, which unit may communicate with the implantable medical device 20 by means of, for example, Bluetooth. In these case, the patient may thus initiate such an ischemia detection procedure by sending a request to the implanted device. In addition, the external device may be a remote monitoring device, such as a PC, located at a care institution in which case the communication may take place via a communication network such as the Internet, GSM or WCDMA, or via telephone link. Accordingly, the physician may send a request to the implanted device. Then, at step S501, signals indicative of a ischemic episode are monitored, i.e. impedances of cardiac tissue. This monitoring, i.e. the measuring or sensing sessions can be initiated at periodic intervals or can be performed continuously. To elaborate, electrical signals to be applied between electrodes of respective electrode configurations including at least a first electrode and at least a second electrode according to a predetermined scheme are generated and the impedances in the tissue between the at least first electrode and the at least second electrode of the electrode configurations to the applied electrical signals are measured according to the predetermined scheme. The impedances hence are measured in accordance with a predetermined measurement scheme, which may be stored in an internal memory of impedance measuring circuit 29 or in the memory circuit 31, and a buffered in successive impedance matrices in the impedance measuring circuit 29 or the ischemia detector 30.

At step S502, a determination is constantly, or at regular intervals, made in the ischemia detector 30 as to whether there have been any changes in the impedances being monitored of sufficient magnitude to indicate the possibility of an occurrence of an ischemic episode. If no changes, or if the magnitude of the changes is too small, the procedure proceeds to step S507, where it is checked whether the monitoring sequence should be continued. Conditions used when to judge whether the monitoring sequence should be continued or not may be whether a monitoring period has elapsed or not, or whether a predetermined number of cardiac cycles has been monitored. If it is determined that the monitoring sequence should be terminated, the procedure proceeds to step S508 where the procedure is terminated. On the other hand, if it is determined that the monitoring sequence should be continued, the procedure returns to step S501 where the monitoring of the impedance is continued. According to an embodiment, the procedure waits for a predetermined period of time before it returns to step S501.

On the other hand, if, at step S501, a change that indicates the occurrence of a myocardial infarction is detected, the procedure proceeds to step S503 where reference impedance images are obtained. The reference impedance images may be predetermined images stored in, for example, an internal memory of the ischemia detector 30 or the in the memory 31 of the implantable medical device 20, or images obtained and created by using measurements performed during a period when no myocardial indicative change in the monitored signals is detected, i.e. during normal conditions, and at provoked ischemic episodes, respectively, and by the reconstruction algorithms as discussed above. These created reference impedance images may be updated periodically. Then, at step S504, the obtained data is evaluated in the ischemia detector 30 including, at step S505, comparing the measured impedances, i.e. the impedance matrices, with the reference impedance images, i.e. the images at normal conditions and at an ischemic episode, of the heart comprising a number of impedance regions to detect changes in the measured impedances being consistent with an ischemia and to determine a location of the ischemia to at least one of the regions. The impedance images can be mapped onto the heart and if changes in the measured impedances being consistent with an ischemia is detected in one or some of the regions, the ischemia can be determined to have occurred in this or these particular region or regions. The ischemia detection will be discussed in further detail below with reference to FIGS. 6a-6c. If an ischemic episode is identified and the location is determined to at least one of the impedance regions, the monitoring sequence proceeds to step S508 where it is terminated. Optionally, the monitoring sequence will include a step S506 in which a notification or warning including the ischemia data, e.g. including the identification of the ischemia, the point of time at which the ischemia episode was identified and the location of the episode, is transferred to one or more external devices, for example, a user equipment, a home monitoring unit, a remote monitoring unit or a emergency server at a care institution or the local hospital via a communication unit of the medical device and at least one external radio communication network such as wireless LAN ("Local Area Network"), GSM ("Global System for Mobile communications"), or UMTS ("Universal Mobile Telecommunications System"). For a given communication method, a multitude of standard and/or proprietary communication protocols may be used. For example, and without limitation, wireless (e.g. radio frequency pulse coding, spread spectrum frequency hopping, time-hopping, etc.) and other communication protocols (e.g. SMTP, FTP, TCP/IP) may be used. Other proprietary methods and protocols may also be used. The notification may include at least the patient identity, the occurrence of a myocardial infarction and/or the location of the detected infarct within the heart. The communication unit may be adapted to communicate with the user equipment, e.g. mobile phone, a pager or a PDA ("Personal Digital Assistant"), which is adapted to receive the notification and to transmit it via the communication network further to the medical care institution. Alternatively, the communication unit may be adapted to communicate with a home monitoring unit located in the home of the patient. The home monitoring unit may be adapted to communicate with the care institution via a telephone link, or via the communication network as described above. Furthermore, the notification may include a geographical location of the patient, for example, by means of a GPS ("Global Positioning System") unit arranged in the user equipment. Thereby, it is possible for the care institution to obtain an early notification of the infarct of a patient and, additionally, the position of the patient and hence the patient can be given care at an early stage of an ischemia. If no ischemic episode is identified during the evaluation, the procedure proceeds to step S507, where it is checked whether the monitoring sequence should be continued as described above.

Figure 6A:
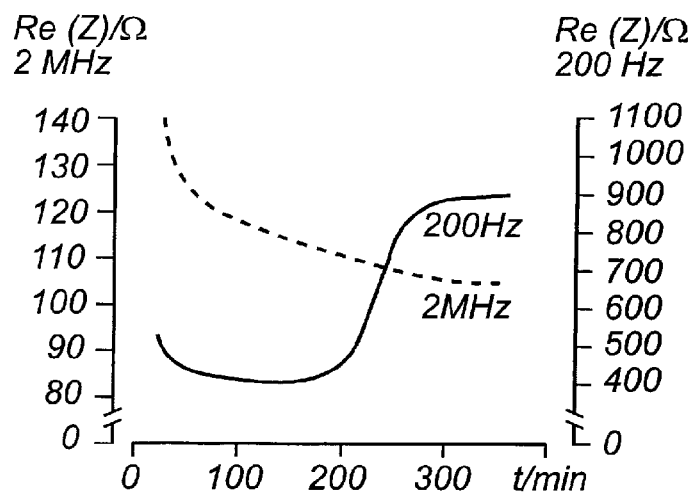
FIG. 6a is a diagram illustrating the real part of the impedance at 2 MHz and 200 Hz over time.
Figure 6B:
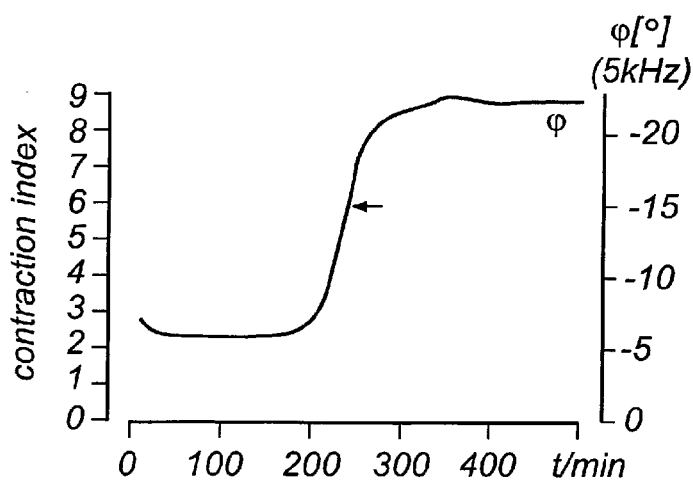
FIG. 6b is a diagram illustrating the phase angle at 5 kHz over time.
Figure 6C:
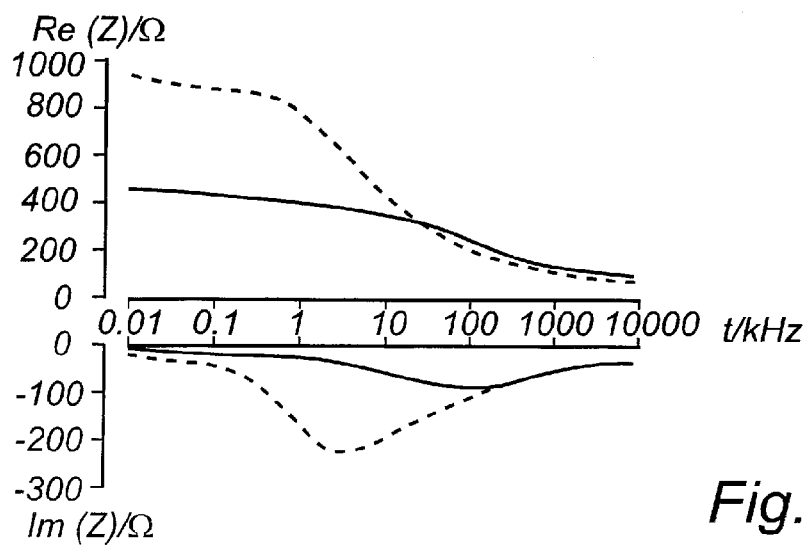
FIG. 6c is a diagram illustrating impedance spectrum at two time points over a frequency band.

With reference now to FIGS. 6a-6c, the detection and localization of ischemia will be discussed in more detail. FIG. 6a illustrates impedance spectra of canine myocardium over time from commencement of an ischemic episode at 200 Hz (indicated with the broken line) and 2 MHz (indicated with the continuous line), FIG. 6b illustrates the phase angle over time at 5 kHz, and FIG. 6c shows impedance spectrum of canine myocardium over frequency at 35 minutes (indicated with the continuous line) and 300 minutes (indicated with the dashed line), respectively, from commencement of an ischemic episode.

According to an embodiment, the impedance at a first and at a second frequency are evaluated, for example, at 200 Hz or at 2 MHz and, thus, the impedance measuring circuit 29, 49 is adapted to apply electrical current pulses at these frequencies in accordance with the predetermined scheme as discussed above. The ischemia detector 30 is adapted to determine a trend of the real part of the measured impedance over time of the measured impedance over time for each region of the impedance image. An increase in the real part of the impedance over time within a predetermined period of time above a first predetermined threshold within a predetermined interval of time below a second predetermined threshold is determined as being consistent with an ischemia, which is indicated in FIG. 6a. As can be seen, the impedance rises significantly and linearly from about 450Ω to about 850Ω in about 50 minutes at 200 Hz, but decreases only slightly from about 725Ω to about 650Ω during the same period of time. A location of the ischemia may, for example, be determined to a region, or regions, for which a time derivative of the real part is above the first predetermined threshold. Alternatively, the region having the highest time derivative of the real part may be determined to be the region in which the ischemia has its origin. In another embodiment, the imaginary part over time is also studied to increase the accuracy. As can be seen in FIG. 6c, the imaginary part of the impedance has shifted from, at 200 Hz, about −20Ω to about −100Ω.

In a further embodiment of the present invention, the impedance at a first frequency and at a second frequency are evaluated, for example, at 500 Hz and at 2 kHz and, thus, the impedance measuring circuit 29, 49 is adapted to apply electrical current pulses at these frequencies in accordance with the predetermined schema as discussed above. The ischemia detector 30 is adapted to determine a trend of the real part of the measured impedance at the first frequency and at the second frequency, respectively, over time and/or a trend of the imaginary part of the measured impedance at the first frequency and the second frequency, respectively, over time for each region of the impedance image.

In one embodiment, the real part at the first frequency and the second frequency, respectively, at a predetermined point of time is compared, for example, at initiation of a measurement session and after about 265 minutes and/or the imaginary part at the first frequency and the second frequency, respectively, are compared at the predetermined points of time. An absolute value of a quotient between the real part at the first frequency and the real part at the second frequency being above a first predetermined quote threshold and/or an absolute value of a quotient between the imaginary part at the first frequency and the imaginary part at the second frequency being above a second predetermined quotient threshold is determined as being consistent with an ischemia. As can be seen in FIG. 6c, both the real part and the imaginary part shift significantly over time at, for example, 500 Hz and 2 kHz. A location of ischemia can be determined to at least one region for which the absolute value of the quotient between the real part at the first frequency and the real part at the second frequency is above a first predetermined quotient threshold and/or the absolute value of the quotient between the imaginary part at the first frequency and the imaginary part at the second frequency is above a second predetermined quote threshold.

In an alternative embodiment, the ischemia detector is adapted to determine a location of the ischemia to a region for which the absolute value of the quotient between the real part at the first frequency and the real part at the second frequency is the highest and/or the absolute value of the quotient between the imaginary part at the first frequency and the imaginary part at the second frequency is the highest.

In yet another embodiment, the impedance at a predetermined frequency is evaluated, for example, at 5 kHz and, thus, the impedance measuring circuit 29, 49 is adapted to apply electrical current pulses at that frequency in accordance with the predetermined scheme as discussed above. The ischemia detector is adapted to determine a trend of the phase angle of the impedance at the predetermined frequency over time for each region of the impedance image and to determine an increase of the phase angle within a predetermined interval of time above a predetermined threshold as being consistent with an ischemia. In FIG. 6B, the phase angle over time at 5 kHz is illustrated and, as can be seen, there is a significant increase from about 5 degrees at about 200 minutes from commencement of an ischemia to about 20 degrees at about 250 minutes from the commencement of the ischemia. The location of the ischemia may be determined to at least one region for which a time derivative of the phase angle is above the predetermined threshold. Alternatively, the region having the highest time derivative of the phase angle may be determined to be the region in which the ischemia has its origin.

As those skilled in the art will appreciate, and as implicated by the discussion given above with reference to FIGS. 6a-6c, there a number of other conceivable way of determining whether changes in measured impedances are consistent with an ischemia and to determine a location of the ischemia. For example, the impedance measuring circuit may be adapted to measure the impedance over a frequency band and the ischemia detector may be adapted to detect whether changes in the measured impedances are consistent with an ischemia by comparing the measured impedances over the frequency band with reference impedance images of the heart over the frequency band and to determine a location of the ischemia to at least one of the regions, for example, by identifying the region or the regions having the most significant change or changes.

Although modifications and changes may be suggested by those skilled in the art, it is the intention of the inventor to embody within the patent warranted heron all changes and modifications as reasonably and properly come within the scope of his or her contribution to the art.

I claim as my invention:

1. An implantable medical device comprising:
a pulse generator that emits cardiac stimulation pulses;
at least one medical lead connected to said pulse generator that delivers said stimulating pulses in vivo to cardiac tissue of a heart of a patient;
an impedance measuring circuit that, during impedance measurement sessions, generates electrical signals applied between at least a first electrode and a second electrode, among electrodes carried by said at least one medical lead, in at least two electrode configurations according to a predetermined scheme, and that measures impedance in the tissue between said first electrode and said second electrode of each of said at least two electrode configurations; and
an ischemia detector that evaluates the measured impedances by comparing the measured impedances with at least one reference impedance image of the heart comprising a plurality of impedance regions, to detect changes in the measured impedances that are consistent with ischemia, and that determines a location of said ischemia with respect to at least one of said regions.

2. The medical device according to claim 1, wherein said ischemia detector is configured to create a present impedance image using said measured impedance values and to compare said present impedance image with said reference impedance images to detect changes in said measured impedances being consistent with an ischemia and to determine a location of said ischemia to at least one of said regions.

3. The medical device according to claim 1, wherein said impedance measuring circuit is configured to perform reference measurement sessions to obtain reference impedances for said electrode configurations in accordance with said predetermined scheme;
and wherein said medical device further comprises a storage unit that stores said measured reference impedances in an reference impedance matrix; and
wherein said ischemia detector is configured to create said reference impedance images of said heart using said reference impedance matrix and to store said impedance images.

4. The medical device according to claim 3, wherein said ischemia detector is configured to create said impedance images using a reconstruction algorithm.

5. The medical device according to claim 1, wherein said electrodes located in at least one position selected from the group consisting of a coronary vein on the left ventricle or left atrium, in the right atrium, in the right ventricle, in or at the epicardium, on a housing of said medical device.

6. The medical device according to claim 1, wherein said impedance measuring circuit is configured to generate electrical signals at least at a first frequency and at a second frequency and to measure the impedance in the tissue between said at least a first electrode and said at least a second electrode of said electrode configurations at said at least first frequency and said at least second frequency.

7. The medical device according to claim 1, wherein said ischemia detector is configured to:
evaluate said measured impedances including comparing said measured impedances at said first frequency with impedance images for said first frequency of said heart each including a number of impedance regions and comparing said measured impedances at said second frequency with impedance images for said second frequency of said heart each including a number of impedance regions, said regions of said impedance images at said second frequency substantially corresponding to said regions of said impedance images at said first frequency; and detect changes in said measured impedances being consistent with an ischemia and to determine a location of said ischemia to at least one of said regions.

8. The medical device according to claim 7, wherein
said impedance measuring circuit configured to perform at least one reference measurement session to obtain reference impedances for said electrode configurations at said first frequency and at said second frequency; and wherein said medical device further comprises a storage unit that stores said measured reference impedances in a first reference impedance matrix containing impedances at said first frequency and in a second reference impedance matrix at said second frequency; and wherein said ischemia detector is configured to create impedance images of said heart using said reference impedance matrices and to store said impedance images.

9. The medical device according to claim 6, wherein said impedance measuring circuit is configured to generate electrical signals across a band of frequencies including said first and second frequencies.

10. The medical device according to claim 1, wherein
said impedance measuring circuit is configured to perform said impedance measurement sessions at predetermined intervals; and wherein said ischemia detector is adapted to evaluate said measured impedances at said predetermined intervals to determine a trend over time for said measured impedances for respective region of said impedance image.

11. The medical device according to claim 1, wherein said ischemia detector is configured to:

determine a trend of the real part of the measured impedance over time and/or a trend of the imaginary part of the measured impedance over time;

determine an increase in said real part of said impedance over time within a predetermined period of time above a first predetermined threshold and/or a decrease in said imaginary part within a predetermined interval of time below a second predetermined threshold as being consistent with an ischemia; and determine a location of said ischemia to at least one region for which a time derivative of said real part is above said first predetermined threshold and/or a time derivative of said imaginary part of said impedance is below said second predetermined threshold.

12. The medical device according to claim 11, wherein said ischemia detector is configured to determine a location of said ischemia to a region for which a time derivative of said real part is the highest and/or a time derivative of said imaginary part of said impedance is the lowest.

13. The medical device according to claim 10, wherein said ischemia detector is configured to:

determine a trend of the real part of the measured impedance at said first frequency and said second frequency, respectively, over time and/or a trend of the imaginary part of the measured impedance at said first frequency and said second frequency, respectively, over time, said first frequency being lower than said second frequency;

compare said real part at said first frequency and said second frequency, respectively, at a predetermined point of time and/or compare said imaginary part at said first frequency and said second frequency, respectively, at said predetermined point of time;

determine an absolute value of a quote between said real part at said first frequency and said real part at said second frequency being above a first predetermined quote threshold and/or an absolute value of a quotient between said imaginary part at said first frequency and said imaginary part at said second frequency being above a second predetermined quotient threshold as being consistent with an ischemia; and determine a location of said ischemia to at least one region for which said absolute value of said quotient between said real part at said first frequency and said real part at said second frequency is above a first predetermined quotient threshold and/or said absolute value of said quote between said imaginary part at said first frequency and said imaginary part at said second frequency is above a second predetermined quote threshold.

14. The medical device according to claim 10, wherein said ischemia detector is configured to determine a location of said ischemia to a region for which said absolute value of said quotient between said real part at said first frequency and said real part at said second frequency is the highest and/or said absolute value of said quotient between said imaginary part at said first frequency and said imaginary part at said second frequency is the highest.

15. The medical device according to claim 1, and wherein said ischemia detector is configured to:

wherein said ischemia detector is adapted to evaluate said measured impedances at said predetermined intervals to determine a trend over time for said measured impedances for respective region of said impedance image determine a trend of the phase angle of the impedance at a predetermined frequency over time;

determine an increase of said phase angle within a predetermined interval of time above a predetermined threshold as being consistent with an ischemia; and determine a location of said ischemia to at least one region for which a time derivative of said phase angle is above said predetermined threshold.

16. The medical device according to claim 15, wherein said ischemia detector is configured to determine a location of said ischemia to a region for which a time derivative of said phase angle is the highest.

17. The medical device according to claim 1, further comprising:

an activity sensor configured that measures an activity level of said patient; and wherein said ischemia detector is configured to determine whether said measured activity level is below a predetermined activity level limit and to use this determination when evaluating said measured impedances.

18. The medical device according to claim 1 wherein said impedance measuring circuit comprises a timing circuit that synchronizes said impedance measurements with cardiac cycles of said patient such that said impedance measurements are performed at substantially the same point of time in said cardiac cycles.

19. The medical device according to claim 18, wherein said timing circuit causes the impedance measurements to be performed during end-diastole.

20. The medical device according to claim 1, wherein said impedance measuring circuit is configured to perform each impedance measurement session over a predetermined number of consecutive cardiac cycles and to calculate each impedance value as a mean value over said predetermined number of cardiac cycles.

21. The medical device according to claim 1, further comprising:
a posture detecting circuit connected to said impedance measuring circuit and being configured to detect at least a predetermined posture of said patient; and
wherein said impedance measuring circuit is configured to initiate said impedance measuring sessions when said patient is in said at least one predetermined posture.

22. A method for operating an implantable medical device including a pulse generator that emits cardiac stimulating pulses and is connected to at least one medical lead for delivering said pulses in vivo to cardiac tissue of a heart of a patient, comprising the steps of:
generating, during impedance measurement sessions, electrical signals to be applied between at least a first electrode and at least a second electrode among electrodes carried by said at least one medical lead in at least two electrode configurations according to a predetermined scheme;
measuring the impedances in the tissue between said at least first electrode and said at least second electrode of said at least two electrode configurations to the applied electrical signals; and
evaluating said measured impedance values including comparing said measured impedances with at least one reference impedance image of said heart comprising a number of impedance regions to detect changes in said measured impedances being consistent with an ischemia and to determine a location of said ischemia to at least one of said regions.

23. The method according to claim 22, further comprising the step of creating (S504) a present impedance image using said measured impedance values and wherein the step of evaluating comprises comparing said present impedance image with said reference impedance images to detect changes in said measured impedances being consistent with an ischemia and to determine a location of said ischemia to at least one of said regions.

24. The method according to claim 21 further comprising the steps of:
performing a reference measurement session to obtain reference impedances for said electrode configurations in accordance with said predetermined scheme;
storing said measured reference impedances in an reference impedance matrix; and
wherein said step of creating said reference impedance images of said heart using said reference impedance matrix and to store said impedance images.

25. The method according to claim 1, comprising of creating said impedance images using a reconstruction algorithm.

26. The method according to any one of preceding claim 21, placing said electrodes on said at least one medical lead at a position selected from the group consisting of a coronary vein on the left ventricle or left atrium, in the right atrium, in the right ventricle, in or on the epicardium, and on the can of said medical device.

27. The method according to claim 21, wherein the step of generating comprises generating electrical signals at least at a first frequency and at a second frequency and wherein said step of measuring comprises measuring the impedance in the tissue between said at least a first electrode and said at least a second electrode of said electrode configurations at said at least first frequency and said at least second frequency.

28. The method according to claim 26, wherein the step of evaluating further comprises:
evaluating said measured impedances including comparing said measured impedances at said first frequency with impedance images for said first frequency of said heart each including a number of impedance regions; and
comparing said measured impedances at said second frequency with impedance images for said second frequency of said heart each including a number of impedance regions, said regions of said impedance images at said second frequency substantially corresponding to said regions of said impedance images at said first frequency, to detect changes in said measured impedances being consistent with an ischemia and to determine a location of said ischemia to at least one of said regions.

29. The method according to claim 27, further comprising:
performing at least one reference measurement session to obtain reference impedances for said electrode configurations at said first frequency and at said second frequency;
storing said measured reference impedances in a first reference impedance matrix containing impedances at said first frequency and in a second reference impedance matrix at said second frequency; and
wherein said step of creating comprises creating reference impedance images of said heart using said reference impedance matrices and to store said impedance images.

30. The method according to claim 26, wherein the step of generating comprises generating electrical signals across a band of frequencies including said first and second frequencies.

31. The method according to claim 21, further comprising:
performing said impedance measurement sessions at predetermined intervals; and
wherein the step of evaluating comprises evaluating said measured impedances at said predetermined intervals to determine a trend over time for said measured impedances for respective region of said impedance image.

32. The method according to claim 30, wherein said step of evaluating further comprises the steps of:
determining a trend of the real part of the measured impedance over time and/or a trend of the imaginary part of the measured impedance over time;
determining an increase in said real part of said impedance over time within a predetermined period of time above a first predetermined threshold and/or a decrease in said imaginary part within a predetermined interval of time below a second predetermined threshold as being consistent with an ischemia; and
determining a location of said ischemia to at least one region for which a time derivative of said real part is above said first predetermined threshold and/or a time derivative of said imaginary part of said impedance is below said second predetermined threshold.

33. The method according to claim 32, wherein the step of determining a location comprises determining a location of said ischemia to a region for which a time derivative of said real part is the highest and/or a time derivative of said imaginary part of said impedance is the lowest.

34. The method according to claim 30, wherein the step of evaluating further comprises the steps of:
determining a trend of the real part of the measured impedance at said first frequency and said second frequency, respectively, over time and/or a trend of the imaginary part of the measured impedance at said first frequency and said second frequency, respectively, over time, said first frequency being lower than said second frequency;
comparing said real part at said first frequency and said second frequency, respectively, at a predetermined point of time and/or compare said imaginary part at said first frequency and said second frequency, respectively, at said predetermined point of time;

determining an absolute value of a quotient between said real part at said first frequency and said real part at said second frequency being above a first predetermined quotient threshold and/or an absolute value of a quotient between said imaginary part at said first frequency and said imaginary part at said second frequency being above a second predetermined quotient threshold as being consistent with an ischemia; and determining a location of said ischemia to at least one region for which said absolute value of said quotient between said real part at said first frequency and said real part at said second frequency is above a first predetermined quotient threshold and/or said absolute value of said quotient between said imaginary part at said first frequency and said imaginary part at said second frequency is above a second predetermined quotient threshold.

35. The method according to claim 34, wherein said step of determining a location comprises determining a location of said ischemia as a region for which said absolute value of said quotient between said real part at said first frequency and said real part at said second frequency is the highest and/or said absolute value of said quotient between said imaginary part at said first frequency and said imaginary part at said second frequency is the highest.

36. The method according to claim 30, wherein the step of evaluating further comprises the steps of:

determining a trend of the phase angle of the impedance at a predetermined frequency over time;

determining an increase of said phase angle within a predetermined interval of time above a predetermined threshold as being consistent with an ischemia; and determining a location of said ischemia to at least one region for which a time derivative of said phase angle is above said predetermined threshold.

37. The method according to claim 35, wherein the step of determining a location comprises determining a location of said ischemia as a region for which a time derivative of said phase angle is the highest.

38. The method according to claim 21, further comprising the steps of:

measuring an activity level of said patient;

determining whether said measured activity level is below a predetermined activity level limit; and using this determination when evaluating said measured impedances.

39. The method according to claim 21, further comprising:

synchronizing said impedance measurements with cardiac cycles of said patient such that said impedance measurements are performed at substantially the same point of time in said cardiac cycles.

40. The method according to claim 39, comprising performing the impedance measurements are performed during end-diastole.

41. The method according to claim 21, further comprising the steps of:

performing each impedance measurement session over a predetermined number of consecutive cardiac cycles; and calculating each impedance value as a mean value over said predetermined number of cardiac cycles.

42. The medical device according to claim 21, further comprising the steps of:

detecting at least a predetermined posture of said patient; and initiating said impedance measuring sessions when said patient is in said at least one predetermined posture.

43. A computer-readable medium encoded with programming instructions, said medium being loadable into a control unit of a medical device comprising a pulse generator that emits cardiac stimulating pulses and that is connected to at least one medical lead for delivering said pulses in vivo to cardiac tissue of a heart of a patient, and an impedance measuring circuit and a processor, said programming instructions causing said control unit to:

operate said impedance circuit, during impedance measurement sessions, to apply electrical signals between at least a first electrode and at least a second electrode among electrodes carried by said at least one medical lead in at least two electrode configurations according to a predetermined scheme;

operate said impedance circuit to measure impedances in tissue between said first electrode and said second electrode in each of said at least two electrode configurations; and operate said processor to evaluate the measured impedances by comparing the measured impedances with at least one reference impedance image of the heart comprising a plurality of impedance regions, to detect changes in the measured impedances that are consistent with ischemia, and to determine a location of said ischemia relative to at least one of said regions.

* * * * *